United States Patent [19]

Bennett, deceased

[11] Patent Number: Plant 7,190

[45] Date of Patent: Mar. 13, 1990

[54] MINIATURE ROSE PLANT NAMED 'ZELDA LLOYD'

[76] Inventors: Cecilia L. D. Bennett, deceased, late of Chula Vista; by Susan M. O'Brien, executrix, 489 Minot Ave., Chula Vista, both of Calif. 92010

[21] Appl. No.: 293,174

[22] Filed: Jan. 3, 1989

[51] Int. Cl.[4] ..... A01H 5/00

[52] U.S. Cl. ..... Plt./9

[58] Field of Search ..... Plt./9

*Primary Examiner*—James R. Feyrer

[57] ABSTRACT

The subject of the present disclosure is a new and distinct variety of miniature rose plant, named 'Zelda Lloyd', which is characterized by its medium pink blooms, ranging from Carmine Rose to Carmellia, with exactly five petals and usually borne one to a stem or in sprays of 3 to 5 or more blooms. The bush is of moderate size and well-branched, producing average to heavy quantities of bloom.

1 Drawing Sheet

The present invention relates to a new and distinct variety of a hardy, dwarf, bush plant of the miniature class; the variety being primarily characterized as medium pink.

The variety is further characterized by:

Long stemmed blooms of five petals only, borne usually one to a stem but on occasion in sprays of 3 to 5 or more. The blooms are held erect and usually above the foliage.

It has a slight amount of fragrance.

The plant ranges is height from 12 to 20 inches (30 to 50 cm). The canes are sturdy and erect with moderate to heavy branching and medium foliage covering. The plant is a moderate to heavy bloomer that does well either in the greenhouse or outdoors.

The plant has good growth habits, well-shaped and attractive, bearing numerous leaflets of average size. I have found this variety to be easily asexually reproduced from cuttings.

The seed parent was Deep Purple (U.S. Plant Pat. No. 4,672), and the pollen parent was Blue Mist (miniature rose plant, mauve; R. S. Moore; introduced by Sequoia Nurseries, 1970). It differs from its seed parent in the following ways. It is a miniature rose with only one row of petals of medium pink, and Deep Purple is a floribunda rose with 30–45 petals of mauve. It differs from its pollen parent in the following ways. It is a five-petaled bloom of medium pink, and Blue Mist has 18–25 petals of mauve.

The descriptive matter which follows pertains to roses grown and color values observed in plants and newly opened blooms in the months of March through November 1988. The plants were grown outdoors in Chula Vista, Calif., and are believed to be accurate standards for this cultivar in similar conditions of soil and climate elsewhere.

BRIEF DESCRIPTION OF THE DRAWING

The single color photographic view shows, in plain view, fully open flowers of 'Zelda Lloyd' in various stages of maturity from early bud stage to nearly full blown stage.

BOTANICAL DESCRIPTION

Referring now specifically to the new and distinct variety of miniature rose plant named 'Zelda Lloyd', the following is a detailed description thereof in outline; all major color plate identifications being by reference to the British Colour Council Horticultural Colour Chart, except where common terms of color definition are employed.

Type: Hardy, dwarf, bushy, greenhouse or outdoor, exhibition or garden decorative potted plant.

Class: Miniature.

Variety Name: Zelda Lloyd.

Flowers borne: Usually one to a stem, but occasionally in sprays of 3 to 5 or more on erect stems with foliage well below the blooms.

Quantity of bloom: Moderate to heavy both outdoors or greenhouse grown.

Bud:

*Peduncle.*—Average length (30 to 50 mm); average diameter and sturdy; ranging from near Scheeles Green (860/3 to 860/1 page 175) to near Lettuce Green (861/3 to 861/1 page 176) with occasional tinting of bronze.

*Hairs.*—None.

*Calyx.*—Color range same as peduncle.

*Opening.*—Opens well in all weather.

Bloom:

*Size when fully open.*—Average for a miniature variety (20 to 30 mm).

*Petalage.*—Single — Five petals arranged regularly with occasional 1 to 3 petaloids.

*Form.*—Urn-shaped bud that opens to a flat five-petaled bloom. No reflexing of the margins is present in the open bloom.

Petals: Fairly thick with good substance; both the upper and under surfaces of all petals have a matte finish.

*Shape.*—All petals are of a very broad obovate form with a slight peak at the apex.

Color: Newly opened flowers from plants grown outdoors (March through November of 1988), Chula Vista, Calif.

*All petals.*—Upper surfaces — Ranging from near Carmine Rose (621/3 to 621/1 page 75) to near Carmellia (622/3 to 622/1 page 148). Under surfaces — Ranging from near Carmine Rose (621/2 to 621 page 75) to near Carmellia (622/2 to 622 page 148). Slight fading of the color may occur with blooms open more than 3 days in warm weather.

*General color effect.*—Newly opened flowers — Rich pink. Three days open — Little or no fading of color. Three to five days open — Fading of color during warm weather, particularly on the outer margins of petals.

*Flower Longevity.*—(March through November of 1988) Plant in pot 1 to 2 days from bud to fully opened bloom. Holding at fully opened with little or no fading of color for 3 to 5 days. Cut blooms at living room temperature 3 to 5 days or longer.

Reproductive organs:

*Stamens.*—A generous amount arranged uniformly around the pistil.

*Filaments.*—Varying in length with shorter filaments more proximal to the pistil; medium pink in color with anthers of golden yellow.

*Pollen.*—Abundant.

*Pistil.*—Short, abundant and compact; pale yellow in color.

*Ovaries.*—All encased in calyx.

*Hips.*—Some.

*Seeds.*—3 to 5 or more in each hip.

*Sepals.*—Permanent; spear-shaped; open and recurve against the peduncle, when the bloom opens.

Foliage:

*Leaves.*—Five to seven leaflets on the average; medium size for a miniature rose plant.

*Leaflets.*—Broad ovate-shaped.

*Margins.*—Very serrated with tinting of bronze, especially noticeable on the newer foliage.

*Color.*—Ranging from near Scheeles Green (860/3 to 860/1 page 175) to near Lettuce Green (861/3 to 861/1 page 176) with occasional bronzing of the margins, especially on the newer foliage. Upper surfaces have a semi-glossy finish, and the under surfaces have a matte finish of a slightly lighter shade than the upper surfaces.

*Rachis.*—Medium strength; upper surface is grooved with very small hairs over the length of it. Under surface has few if any hairs but does contain 2 to 5 small thorns.

*Stipules.*—Varying in length from small to medium; average width; tapering auricles angled outward at about 45 degrees.

Growth:

*Habit.*—Dwarf, bushy; average height for a miniature rose plant.

*Growth.*—Slow to moderate with good branching.

*Canes.*—Medium in diameter; sturdy; held erect.

*Main stems.*—Color range same as foliage.

*Thorns.*—Averaging 5 to 10 per 10 cm on the main stems and few if any on the branches. Pale yellow in color with an occasional tinting of bronze.

*Branches.*—Color — Color range same as foliage.

The miniature rose plant and its flowers as herein described may vary in slight detail due to climate, soil and cultural conditions under which the variety may be grown; the present description being of the variety as grown in Chula Vista, Calif.

The following is claimed:

1. A new and distinct variety of miniature rose plant named, 'Zelda Lloyd' of hardy, dwarf, moderate growth, well-branched and attractive in appearance, substantially as illustrated and described, characterized by its five-petaled blooms of medium pink, ranging from near Carmine Rose to near Carmellia, with flowers borne usually one to a stem but occasionally in sprays of 3 to 5 or more.

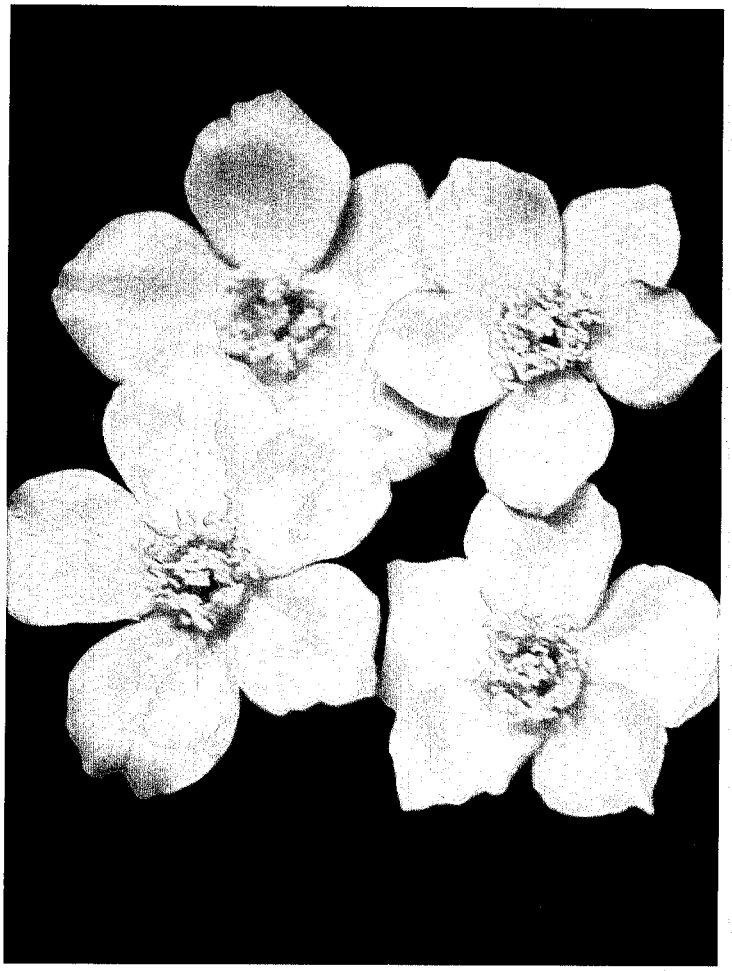

* * * * *